(12) United States Patent
Zaniboni et al.

(10) Patent No.: US 12,280,323 B2
(45) Date of Patent: Apr. 22, 2025

(54) SYSTEMS AND METHODS FOR REMOVING GASEOUS MICRO EMBOLI FROM BLOOD

(71) Applicant: Sorin Group Italia S.r.l., Milan (IT)

(72) Inventors: Andrea Zaniboni, San Martino Spino (IT); Stefano Spro, Calimera (IT); Claudio Silvestri, Quarantoli Mirandola (IT)

(73) Assignee: Sorin Group Italia S.r.l., Milan (IT)

( * ) Notice: Subject to any disclaimer, the term of this patent is extended or adjusted under 35 U.S.C. 154(b) by 499 days.

(21) Appl. No.: 17/688,184

(22) Filed: Mar. 7, 2022

(65) Prior Publication Data

US 2022/0184530 A1 Jun. 16, 2022

Related U.S. Application Data

(63) Continuation of application No. PCT/IB2019/058158, filed on Oct. 3, 2019.

(51) Int. Cl.
*B01D 53/22* (2006.01)
*A61M 1/16* (2006.01)
(Continued)

(52) U.S. Cl.
CPC ....... *B01D 19/0031* (2013.01); *A61M 1/1698* (2013.01); *A61M 1/3623* (2022.05);
(Continued)

(58) Field of Classification Search
CPC ........................ B01D 19/00; B01D 19/0031; B01D 19/0036; B01D 53/22; B01D 53/221;
(Continued)

(56) References Cited

U.S. PATENT DOCUMENTS

| 6,267,926 B1 | 7/2001 | Reed et al. |
| 6,267,936 B1 * | 7/2001 | Delmas ..................... C22B 3/38 |
| | | 423/63 |

(Continued)

FOREIGN PATENT DOCUMENTS

| DE | 102018002385 A1 | 9/2019 |
| EP | 0089122 A2 | 9/1983 |

(Continued)

OTHER PUBLICATIONS

Machine-generated English translation of DE 102018002385 A1, published Sep. 26, 2019.*

(Continued)

*Primary Examiner* — Frank M Lawrence, Jr.
(74) *Attorney, Agent, or Firm* — Seager, Tufte & Wickhem LLP

(57) ABSTRACT

A system for removing gaseous micro emboli from blood prior to oxygenation. The system including a module having a blood inlet, a blood outlet, and a port configured to provide atmospheric or sub-atmospheric pressures, and microporous hollow fibers situated in the module and fluidly coupled to the port to provide the atmospheric or sub-atmospheric pressures inside the microporous hollow fibers. The module is configured to receive the blood through the blood inlet such that the blood flows from the blood inlet to the blood outlet around outside surfaces of the microporous hollow fibers such that at least some of the gaseous micro emboli in the blood are drawn from the blood through the microporous hollow fibers by the atmospheric or sub-atmospheric pressures.

13 Claims, 9 Drawing Sheets

(51) Int. Cl.
*A61M 1/36* (2006.01)
*B01D 19/00* (2006.01)
(52) U.S. Cl.
CPC ........ *A61M 1/3627* (2013.01); *A61M 1/3666* (2013.01); *B01D 19/0036* (2013.01); *B01D 53/22* (2013.01); *A61M 2205/7536* (2013.01)
(58) Field of Classification Search
CPC .. B01D 53/222; B01D 53/223; B01D 53/224; A61M 1/1698; A61M 1/3623; A61M 1/3627; A61M 1/3666; A61M 2205/7536
USPC ............. 95/43, 46, 54, 266; 96/4, 7–10, 193
See application file for complete search history.

(56) References Cited

U.S. PATENT DOCUMENTS

| | | | | |
|---|---|---|---|---|
| 10,792,591 | B2* | 10/2020 | Dyer | .......................... F23K 5/08 |
| 2002/0195385 | A1* | 12/2002 | Cho | ........................ B01D 63/02 |
| | | | | 210/321.74 |
| 2006/0029514 | A1* | 2/2006 | Lindsay | .............. A61M 1/3623 |
| | | | | 422/44 |
| 2006/0081524 | A1 | 4/2006 | Sengupta et al. | |
| 2019/0291457 | A1* | 9/2019 | Yamamoto | .................. B41J 2/18 |
| 2022/0409797 | A1* | 12/2022 | Zaniboni | ............. A61M 1/3627 |

FOREIGN PATENT DOCUMENTS

| | | |
|---|---|---|
| EP | 0374873 A2 | 6/1990 |
| WO | 2019180088 A1 | 9/2019 |

OTHER PUBLICATIONS

International Search Report and Written Opinion for International Application No. PCT/IB2019/058158 dated May 29, 2020.

\* cited by examiner

SYSTEMS AND METHODS FOR REMOVING GASEOUS MICRO EMBOLI FROM BLOOD

CROSS REFERENCE TO RELATED APPLICATIONS

This application is a continuation of International Application No. PCT/IB2019/058158, filed Oct. 3, 2019, the disclosure of which is incorporated herein by reference.

TECHNICAL FIELD

The present disclosure relates to extracorporeal circulation. More specifically, the present disclosure relates to removing gaseous micro emboli from blood in extracorporeal circulation.

BACKGROUND

Generally, in extracorporeal circulation, at least some air is mixed with blood, even though the perfusionist takes great care in limiting the presence of air and removing it as efficiently as possible from the blood. The air may get mixed with the blood in several different ways. One source of air being mixed with blood in extracorporeal circulation includes air aspirated with the blood, by means of one or more suckers, from the operating field and delivered to a venous reservoir, such as a dedicated and separate section of a venous reservoir, i.e., a cardiotomy section, where the blood is then filtered before rejoining extracorporeal circulation. Another source of air being mixed with blood may be due to heart cavity venting, delivered directly to the venous reservoir. A third source of air being mixed with blood includes incorrect sealing of the venous cannula at the cannulation site, where air is aspirated into the blood path due to the negative pressure, provided by gravity or applying a vacuum, needed to drain blood from the patient into the venous reservoir.

The blood mixed with air and collected in a venous/cardiotomy reservoir is filtered to remove at least some of the air. Reservoir filters include both polyurethane sponges loaded with chemical defoamers and surface screens having pore sizes of less than or equal to about 100 microns. These filters remove some of the gross air, but no matter where the air comes from, a significant quantity of the air is fractured inside the reservoir into micro-air bubbles that are much more difficult to remove by filtration. As a result, blood leaving the reservoir towards the oxygenator is not completely free of micro-air bubbles.

Sometimes, in the oxygenator, the oxygenation bed removes some micro-air bubbles by diffusion of the micro-air bubbles through the oxygenation membrane due to the pressure gradient between the blood at a higher pressure on one side of the membrane and the oxygenating gas at a lower pressure on the other side of the membrane. Also, sometimes, downstream of the oxygenator, blood is passed through an arterial filter where micro-air bubbles are trapped and further removed from the blood via filtration that is generally performed by surface filtration through a screen with pore sizes of 20-40 micron.

Despite all these measures being taken to remove air and micro-air bubbles, blood returning to the patient after extracorporeal circulation often or always contains some micro-air bubbles, referred to as gaseous micro emboli (GME). The GME in the blood returning to the patient may cause neurological sequelae in the patient, the most common form being a temporary neurological impairment of the patient disappearing in a few months after the operation, although the damage may sometimes be more severe and permanent.

SUMMARY

In an Example 1, a system for removing gaseous micro emboli from blood prior to oxygenation, the system including: a module having a blood inlet, a blood outlet, and a port configured to provide atmospheric or sub-atmospheric pressures, and microporous hollow fibers situated in the module and fluidly coupled to the port to provide the atmospheric or sub-atmospheric pressures inside the microporous hollow fibers. Wherein the module is configured to receive the blood through the blood inlet such that the blood flows from the blood inlet to the blood outlet around outside surfaces of the microporous hollow fibers such that at least some of the gaseous micro emboli in the blood are drawn from the blood through the microporous hollow fibers by the atmospheric or sub-atmospheric pressures.

Example 2 is the system of Example 1, wherein the sub-atmospheric pressures include pressures down to −400 mmHg vacuum such that 95% or more of the gaseous micro emboli in the blood are drawn from the blood.

Example 3 is the system of Example 1, wherein the module includes a housing and the microporous hollow fibers are wound onto a central cylindrical core in the housing.

Example 4 is the system of Example 1, wherein the module includes a housing and the microporous hollow fibers are stacked in layers that are at least one of horizontally and vertically situated in the housing.

Example 5 is the system of Example 4, wherein the microporous hollow fibers are stacked in layers alternately angled from 0 to 90-degrees in the housing.

Example 6 is the system of Example 1, wherein the module includes a housing and housing end caps with the port situated in one end cap of the housing end caps and at least some of the microporous hollow fibers potted adjacent each of the housing end caps and open at the one end cap to fluidly couple the inside of the at least some of the microporous hollow fibers to the atmospheric or sub-atmospheric pressures provided via the port.

Example 7 is the system of Example 1, wherein the module includes at least one safety valve coupled to the port to exhaust pressures above atmospheric value.

Example 8 is the system of Example 1, wherein the blood received by the module includes venous blood that is processed by the module to draw at least some of the gaseous micro emboli from the venous blood and provide the processed venous blood through the blood outlet to a gas exchanger of an oxygenator.

Example 9 is the system of Example 1, wherein the module provides the blood processed by the module through the blood outlet to an oxygenator that receives oxygenation gases at atmospheric pressure.

Example 10 is the system of Example 1, wherein the module is part of a blood inlet portion of an oxygenator.

In an Example 11, a system for processing blood to remove gaseous micro emboli from the blood and provide processed blood to an oxygenator that receives oxygenation gases at atmospheric pressure to oxygenate the processed blood, the system including: a module having a blood inlet at one side of the module and configured to receive the blood, a blood outlet at another side of the module and configured to output the processed blood, and a port configured to provide gas at atmospheric or sub-atmospheric pressure, and microporous hollow fibers situated in the module and open at one or more ends of the microporous hollow fibers to fluidly couple inside passages of the microporous hollow fibers to the port. Wherein the module receives the blood through the blood inlet and the blood flows from the blood inlet to the blood outlet and around outside surfaces of the microporous hollow fibers to draw at least some of the gaseous micro emboli from the blood through the microporous hollow fibers.

Example 12 is the system of Example 11, wherein the module includes a housing and housing end caps with the port situated in one end cap of the housing end caps and the microporous hollow fibers potted near each of the housing end caps and open at the one end cap to fluidically couple the inside passages of the microporous hollow fibers to the gas at atmospheric or sub-atmospheric pressure.

Example 13 is the system of Example 11, wherein the module includes a housing having a central core and the microporous hollow fibers are wound around the central core in the housing.

Example 14 is the system of Example 11, wherein the module includes a housing and the microporous hollow fibers are stacked in layers at least one of horizontally and vertically situated in the housing.

Example 15 is the system of Example 11, wherein the gas at sub-atmospheric pressure reaches −400 mmHg vacuum, such that 95% or more of the gaseous micro emboli in the blood are drawn from the blood.

In an Example 16, a method of processing blood to remove gaseous micro emboli from the blood prior to oxygenation, the method including: applying atmospheric or sub-atmospheric pressure at a port of a module, the port fluidly coupled to inside passages of microporous hollow fibers in the module; receiving the blood at a blood inlet of the module such that the blood flows from the blood inlet to a blood outlet of the module around outside surfaces of the microporous hollow fibers such that at least some of the gaseous micro emboli in the blood are drawn from the blood through the microporous hollow fibers by the atmospheric or sub-atmospheric pressure; and providing the processed blood through the blood outlet to a gas exchanger for oxygenation.

Example 17 is the method of Example 16, wherein applying atmospheric or sub-atmospheric pressure includes applying a −400 mmHg vacuum such that more than 95% of the gaseous micro emboli in the blood are drawn from the blood.

Example 18 is the method of Example 16, wherein receiving the blood at the blood inlet includes receiving venous blood at the blood inlet and drawing at least some of the gaseous micro emboli from the venous blood.

Example 19 is the method of Example 18, wherein providing the processed blood through the blood outlet includes providing the processed venous blood through the blood outlet to an oxygenator.

Example 20 is the method of Example 16, including receiving oxygenation gases at atmospheric pressure at the gas exchanger to oxygenate the processed blood.

DETAILED DESCRIPTION

Figure 1:
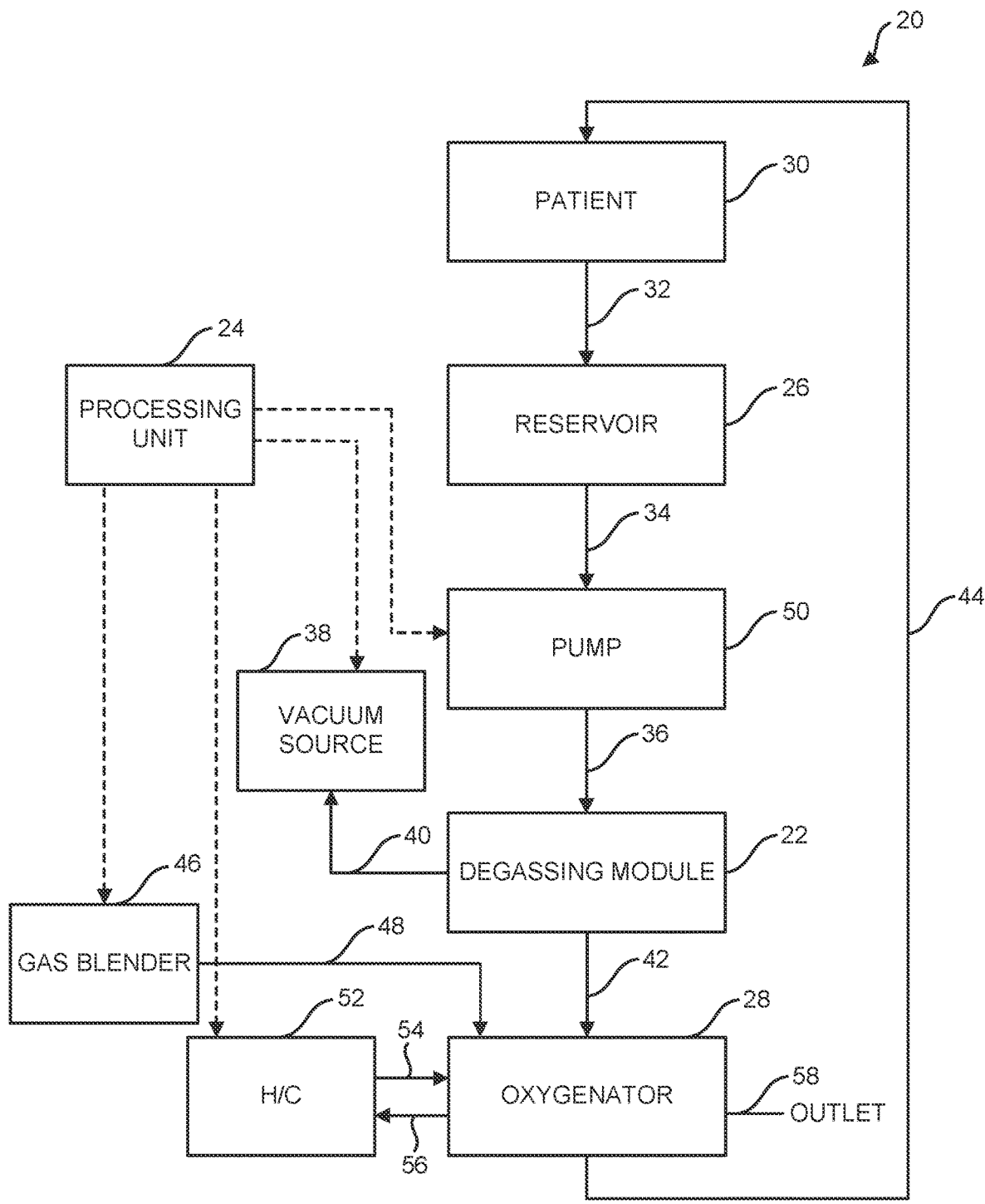
FIG. 1 is a diagram illustrating a system configured to remove GME from blood during extracorporeal circulation, in accordance with embodiments of the subject matter of the disclosure.

FIG. 1 is a diagram illustrating a system 20 configured to remove GME from blood during extracorporeal circulation, in accordance with embodiments of the subject matter of the disclosure. The system 20 includes a blood degassing module 22, also referred to as a GME scavenger, that is configured to remove GME from the blood. In embodiments, the module 22 is dedicated to blood degassing by exploiting one or more of microporous hollow fibers and flat plate hydrophobic microporous membranes, combined with providing a vacuum (at less than atmospheric pressure, i.e., sub-atmospheric pressure) or providing atmospheric pressure, to draw the GME from the blood through the one or more of the microporous hollow fibers and/or the flat plate hydrophobic microporous membranes.

The system 20 includes a processing unit 24, a blood reservoir 26, the blood degassing module 22, and an oxygenator 28. In embodiments, the processing unit 24 may be a heart lung machine (HLM), or part of it, as used in cardiopulmonary bypass surgery. Also, embodiments of the subject matter described herein may be implemented within the context of any number of different processing units, blood reservoirs, and oxygenators.

The processing unit 24 includes components, such as pumps, one or more controller assemblies including computing devices, one or more peripheral display devices, and one or more user interfaces, for providing the functions of the system 20. The functions of the system 20 include receiving blood from a patient 30, providing the received blood to the blood reservoir 26, and supplying the blood from the blood reservoir 26 to the degassing module 22. After being degassed in the degassing module 22, the blood moves on to the oxygenator 28, before going back to the patient 30.

The processing unit 24 is operatively coupled to the patient 30 and to the extracorporeal blood circulation system. Blood is taken from the patient 30 by means of a venous blood tubing line 32 and received by the blood reservoir 26. Besides this, blood may be aspirated into the reservoir 26 by means of one or more suckers from the operating field and be otherwise received into the blood reservoir 26 from the patient 30. In embodiments, the blood reservoir 26 includes a filter for filtering the blood received from the patient 30 and the operating field, prior to passing the blood to the degassing module 22.

The blood degassing module 22 is fluidly coupled to the blood reservoir 26 to receive the blood from the blood reservoir 26. A roller, or centrifugal blood pump 50 that is controlled by processing unit 24 may be interposed between the blood reservoir 26 and the blood degassing module 22. The pump 50 is fluidly coupled to the blood reservoir by blood tubing line 34 and fluidly coupled to the blood degassing module 22 by blood tubing line 36. The pump 50 is used for pumping blood from the outlet port of the blood reservoir 26 through the blood tubing line 34 and to the inlet port of blood degassing module 22 through the blood tubing line 36. The blood degassing module 22 is further fluidly coupled to vacuum source 38 by fluid tubing line 40 for applying a vacuum through the fluid tubing line 40 to the blood degassing module 22. Alternatively, atmospheric pressure may be provided to the blood degassing module 22, such as by keeping the fluid tubing line 40 open to the atmosphere.

The blood degassing module 22 processes the blood by removing GME from the blood due to the pressure differential between the blood pressure and the vacuum or atmospheric pressure applied to the module 22. The module 22 is fluidly coupled to the oxygenator 28 by blood tubing line 42 and provides the processed blood to the oxygenator 28 through the blood tubing line 42. In embodiments, the fluid tubing line 40 provides from atmospheric pressure to a vacuum of –400 mmHg to the blood degassing module 22.

In embodiments, the module 22 includes microporous hollow fibers, with the vacuum or, alternatively, atmospheric pressure provided on one side of the microporous hollow fibers, such as inside the microporous hollow fibers. The blood circulates on the other side of the microporous hollow fibers, such as around the outside surfaces of the microporous hollow fibers, such that the vacuum or atmospheric pressure, being always lower than the blood's pressure, draws GME from the blood to remove at least some of the GME from the blood.

In embodiments, the module 22 includes one or more flat plate hydrophobic microporous membranes and the vacuum or, alternatively, the atmospheric pressure is provided on one side of the flat plate hydrophobic microporous membranes. The blood circulates on the other side of the flat plate hydrophobic microporous membranes, such that the pressure differential between blood, on one side, and atmospheric or sub-atmospheric pressure on the other side, draws GME from the blood to remove at least some of the GME from the blood.

The oxygenator 28 receives the processed blood from the module 22 through the blood tubing line 42 and oxygenates and heats/cools the processed blood before returning the blood to the patient 30 through blood tubing line 44. The oxygenator 28 is operatively coupled to the processing unit 24, which controls the return of the degassed, oxygenated, and temperature-controlled blood to the patient 30 through the blood tubing line 44, such as an arterial line.

In embodiments, the oxygenator 28 is fluidly coupled to a gas mixture module or gas blender 46 by fluid tubing line 48 and to a heater/cooler module 52 by heater/cooler fluid tubing lines 54 and 56. The gas blender 46 provides oxygenation gases to the oxygenator 28 through inlet fluid tubing line 48 to oxygenate the processed blood. The gas outlet 58 of the oxygenator gas is kept fully open to the atmosphere, such that given the pressure losses in the oxygenator gas, oxygenation takes place, as usually happens with all existing oxygenators, with the oxygenation gases at pressure values slightly over or close to atmospheric pressure values. Thus, the blood degassing module 22 provides a more efficient removal of GME, as compared to removal of GME through the oxygenator 28, due to the larger pressure differential between the blood pressure in the module 22, which is higher than in the oxygenator 28, and the vacuum or, alternatively, atmospheric pressure provided to the module 22.

The heater/cooler module 52 provides a fluid, such as water, at a controlled temperature to the oxygenator 28 through inlet fluid tubing line 54 for heating/cooling the blood and the heater/cooler module 52 receives returning fluid through the outlet fluid tubing line 56. In embodiments, one or more of the gas blender 46 and the heater/cooler module 52 are controlled by the processing unit 24.

In embodiments, the module 22 is incorporated into the oxygenator 28. More precisely, the module 22 may be located between the heat exchanger and the gas exchanger, which are often lodged in the same oxygenator housing, or upstream of the heat exchanger of the oxygenator, such as in the blood inlet portion of the oxygenator 28. In embodiments, the module 22 is incorporated into the blood outlet portion of the reservoir 26, such that the blood is processed by the module 22 prior to exiting the reservoir 26. In such a case, the pump 50 is placed between the reservoir outlet port and the oxygenator inlet port.

Figure 2:
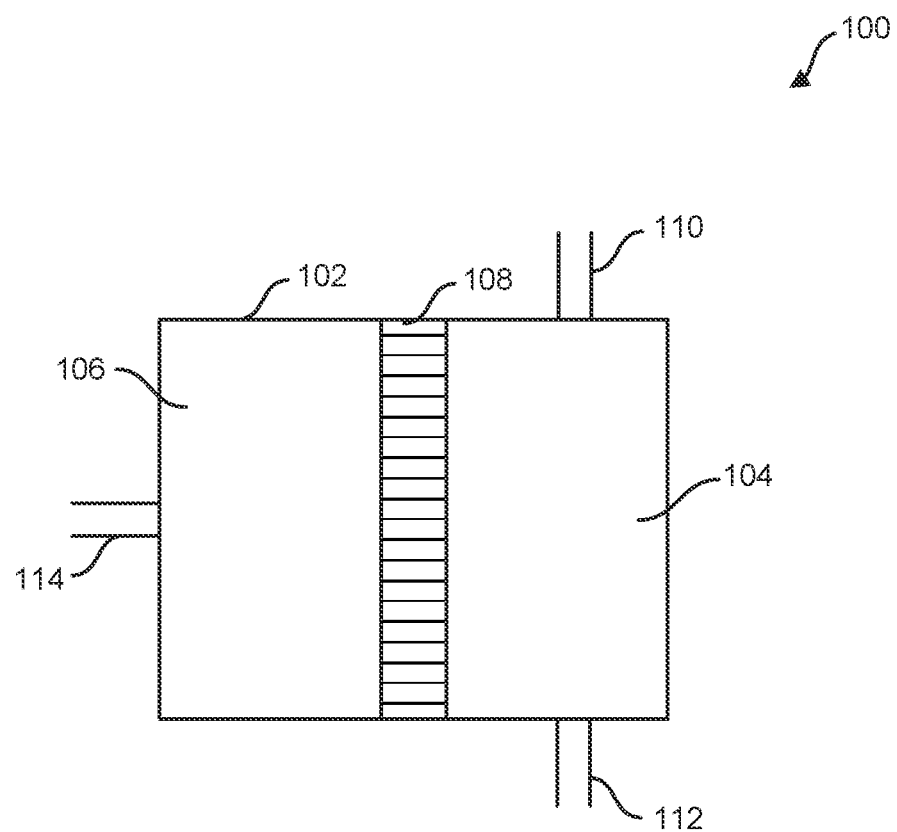
FIG. 2 is a diagram illustrating a blood degassing module, in accordance with embodiments of the subject matter of the disclosure.

FIG. 2 is a diagram illustrating a blood degassing module 100, in accordance with embodiments of the subject matter of the disclosure. In embodiments, the blood degassing module 100 is like blood degassing module 22 (shown in FIG. 1). In embodiments, the blood degassing module 100 can be used in place of blood degassing module 22 in system 20.

The blood degassing module 100 includes a housing 102 that has a blood compartment 104, a vacuum/atmospheric pressure compartment 106, and a microporous hydrophobic membrane 108 that separates the blood compartment 104 and the vacuum/atmospheric pressure compartment 106.

The module 100 includes a blood inlet 110 fluidly coupled to the blood compartment 104, a blood outlet 112 fluidly coupled to the blood compartment 104, and a port 114 fluidly coupled to the vacuum/atmospheric pressure compartment 106. The blood inlet 110 is configured to receive blood, such as venous blood or aspirated blood, and provide the received blood to the blood compartment 104. The received blood flows through the blood compartment 104 and out the blood outlet 112. The port 114 is configured to be kept open to atmospheric pressure or receive a vacuum, i.e., sub-atmospheric pressure, and provide the vacuum or atmospheric pressure to the vacuum/atmospheric pressure compartment 106. In embodiments, the blood outlet 112 is configured to be coupled to an oxygenator for oxygenating the blood after gross air and GME have been removed from the blood inside the module 100.

The microporous hydrophobic membrane 108 is configured to pass at least some gross air and GME from the blood to the compartment 106 under atmospheric pressure or a vacuum. In embodiments, the microporous hydrophobic membrane 108 is in the form of hollow fibers. In embodiments, the microporous hydrophobic membrane 108 is in the form of a flat plate membrane. Also, in embodiments, the microporous hydrophobic membrane 108 may be made from or include one or more polypropylene (PP) and polymethylpentene (PMP) materials.

In operation, a mixture of blood and air is circulated through the blood compartment 104 of the module 100 from the blood inlet 110 to the blood outlet 112. In the blood compartment 104, the mixture of blood and air contacts one side of the microporous hydrophobic membrane 108. The other side of the microporous hydrophobic membrane 108 is exposed to the vacuum or atmospheric pressure in the compartment 106, such that the pressure gradient between the two sides of the microporous hydrophobic membrane 108 causes at least some gross air and GME in the blood to cross the microporous hydrophobic membrane 108 and be removed from blood. As a result, processed blood exiting the module 100 has less gross air and GME than the mixture of blood and air entering the module 100 at the blood inlet 110.

Also, in embodiments, the blood degassing module 100 draws gas such as 02 and C02 molecules dissolved in the blood from the blood, such that the processed blood leaving the module 100 is somewhat deprived of C02 and 02 and needs to be oxygenated by circulating it through an oxygenator cascaded with the module 100.

Figure 3:
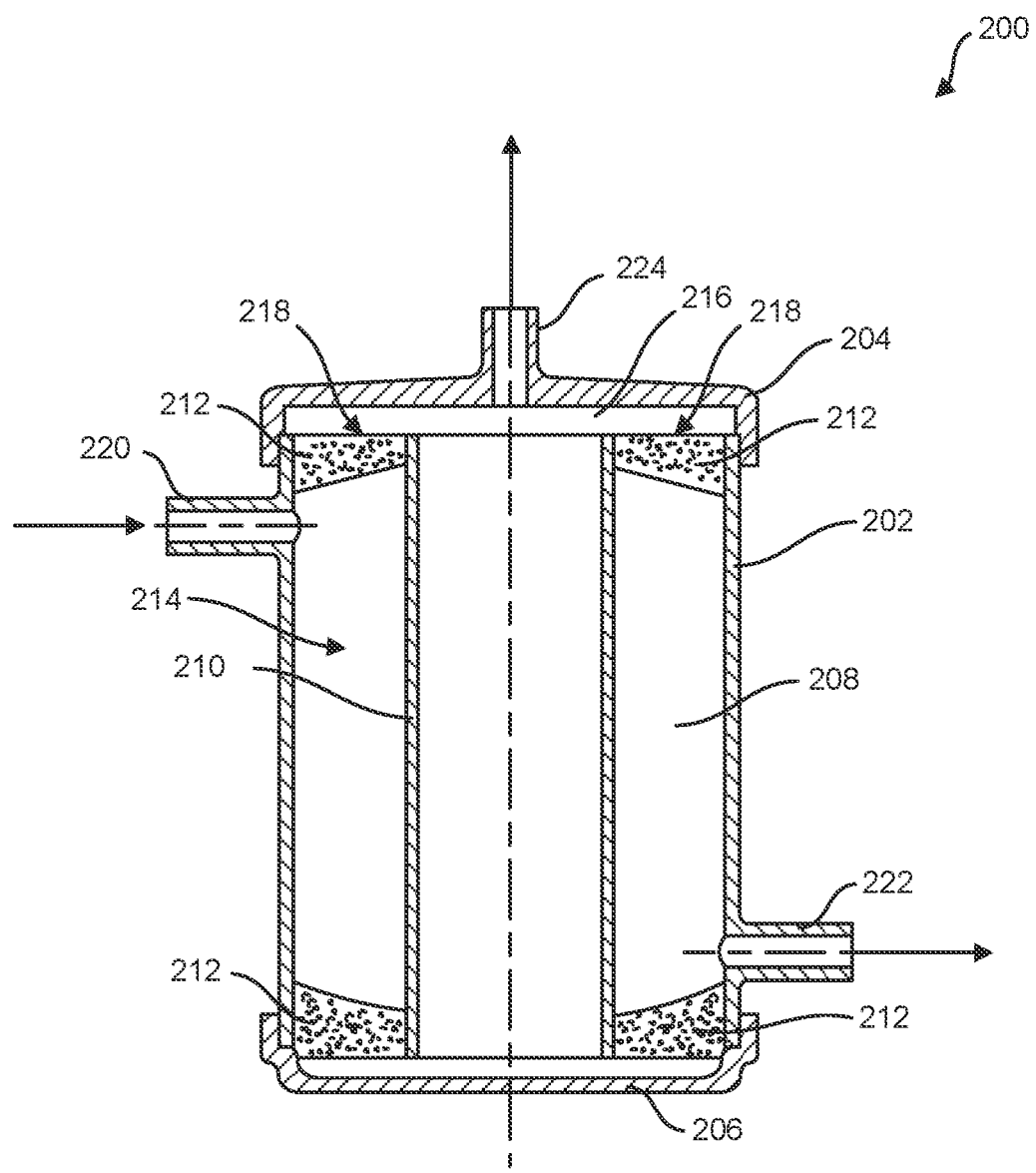
FIG. 3 is a diagram illustrating a blood degassing module, in accordance with embodiments of the subject matter of the disclosure.

FIG. 3 is a diagram illustrating a blood degassing module 200, in accordance with embodiments of the subject matter of the disclosure. In embodiments, the blood degassing module 200 is like blood degassing module 22 (shown in FIG. 1). In embodiments, the blood degassing module 200 can be used in place of blood degassing module 22 in system 20 of FIG. 1. In some embodiments, at least one or more portions of blood degassing module 200 is like blood degassing module 100 of FIG. 2.

The blood degassing module 200 includes a cylindrical housing 202 (shown in cross section in FIG. 3), a first end cap 204 attached to one end of the cylindrical housing 202, and a second end cap 206 attached to the other end of the cylindrical housing 202. The cylindrical housing 202 and the first and second end caps 204 and 206 form an enclosure that houses a membrane in the form of microporous hollow fibers 208 wound around and onto a central core 210. In embodiments, the central core 210 is cylindrical.

In embodiments, the microporous hollow fibers 208 may be one or more of wound singularly around the central core 210, arranged in a single layer around the central core 210, and arranged in a double layer mat, where each layer crosses the other at an angle and is spirally wound around the central core 210. Also, in embodiments, the microporous hollow fibers 208 are made from or at least include one or more of PP and PMP material.

The microporous hollow fibers 208 are wound onto the central core 210 and potted with potting material 212 at each end of the cylindrical housing 202 to form two separate compartments. One compartment is a blood compartment 214 configured to have blood flow through it, such that the blood contacts outer surfaces of the microporous hollow fibers 208. The other compartment is a vacuum/atmospheric pressure compartment 216 configured to be at atmospheric pressure or at less than atmospheric pressure and fluidly coupled to inside surfaces of the microporous hollow fibers 208. In embodiments, the potting material 212 includes a urethane resin.

The microporous hollow fibers 208 are cut open at 218, above the potting material 212 and at the end of the housing 202 adjacent the end cap 204. This fluidly couples the inside surfaces of the hollow fibers 208 to the atmospheric or sub-atmospheric pressure of compartment 216. The microporous hollow fibers 208 are closed off by the potting material 212 at the other end of the housing 202, adjacent the end cap 206. The microporous hollow fibers 208 are configured to draw at least some gross air and GME from blood in the blood compartment 214 to the atmospheric or sub-atmospheric (vacuum) pressure of the compartment 216. In other embodiments, the microporous hollow fibers 208 are not closed off by the potting material 212 at the other end of the housing 202, but left open, adjacent the end cap 206. In other embodiments, the microporous hollow fibers 208 are not closed off by the potting material 212 at the other end of the housing 202 adjacent the end cap 206, but left open to compartment 216, which fluidly couples the inside surfaces of the hollow fibers 208 to the atmospheric or sub-atmospheric pressure of compartment 216.

The module 200 includes a blood inlet 220 at one side and at one end of the housing 202, such as adjacent the first end cap 204, and a blood outlet 222 at the other side and at the other end of the housing 202, such as adjacent the second end cap 206. The blood inlet 220 and the blood outlet 222 are each fluidly coupled to the blood compartment 214. The blood inlet 220 is configured to receive blood, such as venous blood or aspirated blood, and provide the received blood to the blood compartment 214. The received blood flows through the blood compartment 214 and out of the blood outlet 222. In embodiments, the blood outlet 222 is configured to be coupled to an oxygenator for oxygenating the blood after gross air and GME have been drawn from the blood.

The first end cap 204 includes a port 224 fluidly coupled to the compartment 216. The port 224 is configured to receive a vacuum, i.e., a sub-atmospheric pressure, or atmospheric pressure and provide it to the compartment 216. In embodiments, the module 200 includes a relief safety valve (not shown) connected to the port 224. The relief safety valve automatically opens the compartment 216 to the atmosphere if, for any reason, the pressure becomes positive in the compartment 216. This prevents possible inversion of the degassing action and air entering the blood.

In operation, blood mixed with some air is circulated through the blood compartment 214 from the blood inlet 220 to the blood outlet 222. The blood flows around the central core 210 and from one end of the housing 202 to the other end of the housing 202. In the blood compartment 214, the mixture of blood and air contacts the outer surfaces of the microporous hollow fibers 208. The inside of the microporous hollow fibers 208 is exposed to the vacuum or gas at atmospheric pressure in the compartment 216, such that the pressure gradient between the two sides of the microporous hollow fibers 208 causes at least some gross air and GME in the blood to cross the microporous hollow fibers 208 and be removed from blood. As a result, processed blood exiting the module 200 at the blood outlet 222 has less gross air and GME than the mixture of blood and air entering the module 200 at the blood inlet 220.

Figure 4:
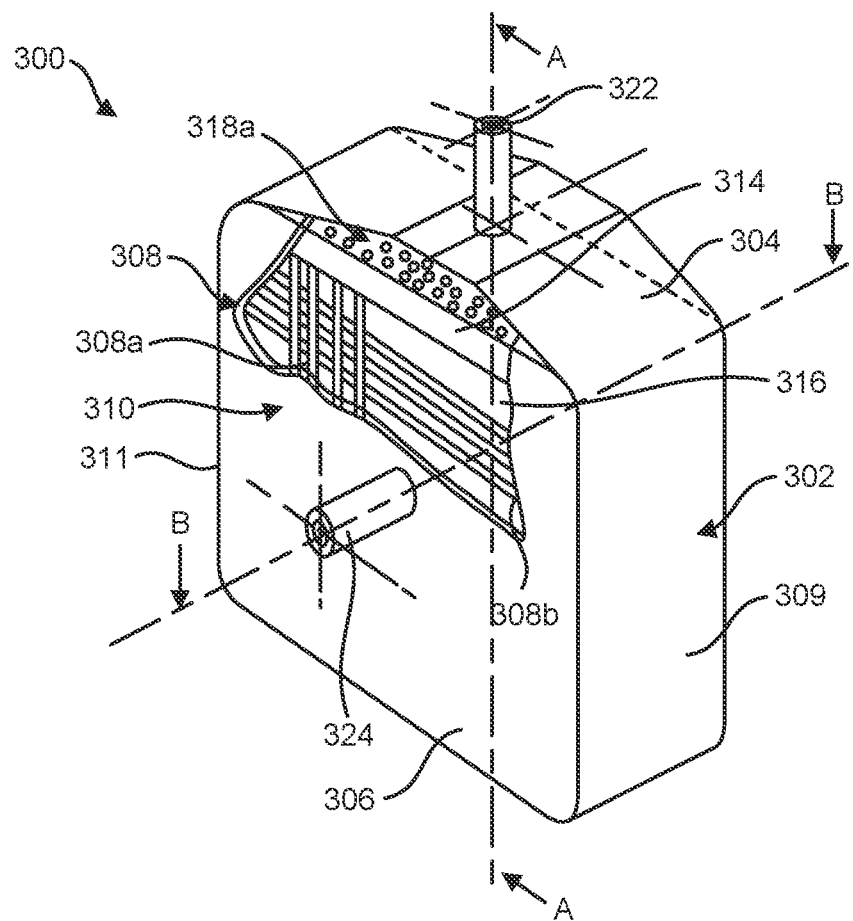
FIG. 4 is a diagram illustrating another blood degassing module, in accordance with embodiments of the subject matter of the disclosure.

FIG. 4 is a diagram illustrating another blood degassing module 300, in accordance with embodiments of the subject matter of the disclosure. In embodiments, the blood degassing module 300 is like blood degassing module 22 (shown in FIG. 1). In embodiments, the blood degassing module 300 can be used in place of blood degassing module 22 in system 20 of FIG. 1. In some embodiments, at least one or more portions of blood degassing module 300 is like blood degassing module 100 of FIG. 2. In some embodiments, at least one or more portions of blood degassing module 300 is like blood degassing module 200 of FIG. 3.

Figure 4A:
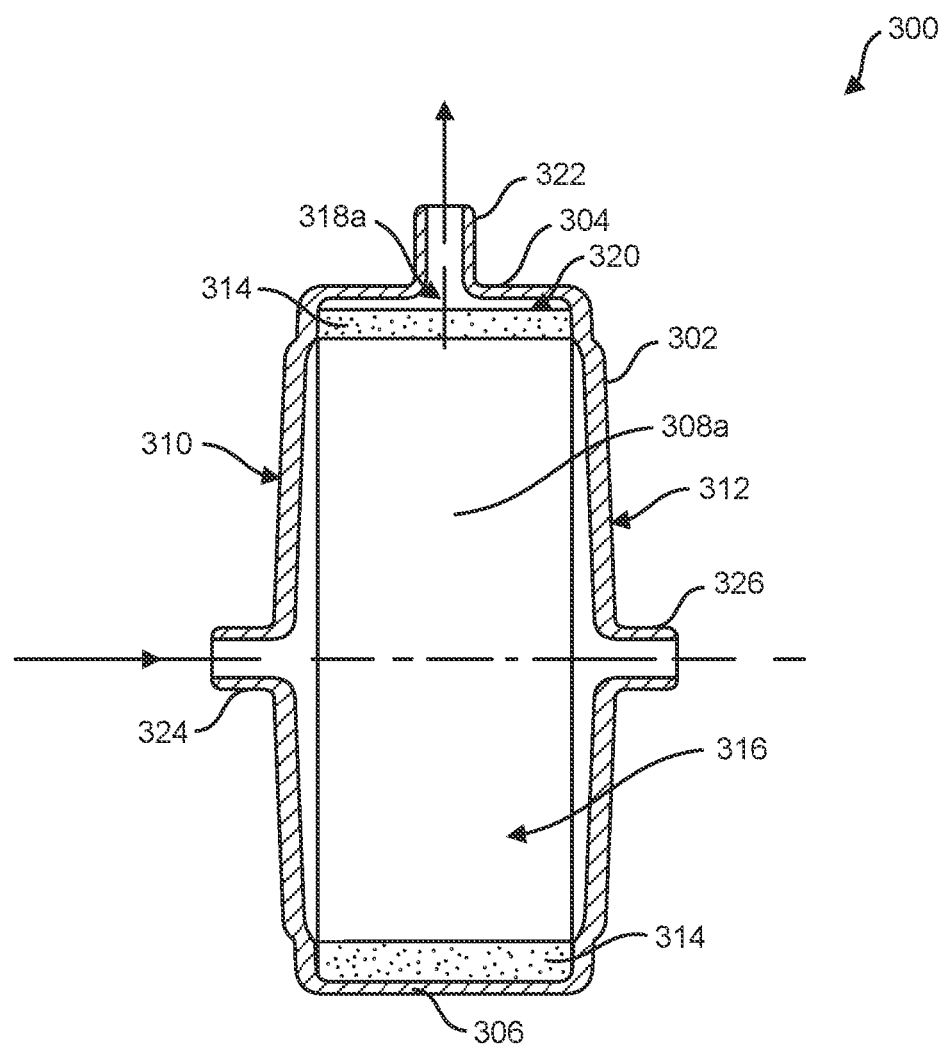
FIG. 4A is a diagram illustrating a cross-section along the lines A-A of the blood degassing module of FIG. 4, in accordance with embodiments of the subject matter of the disclosure.
Figure 4B:
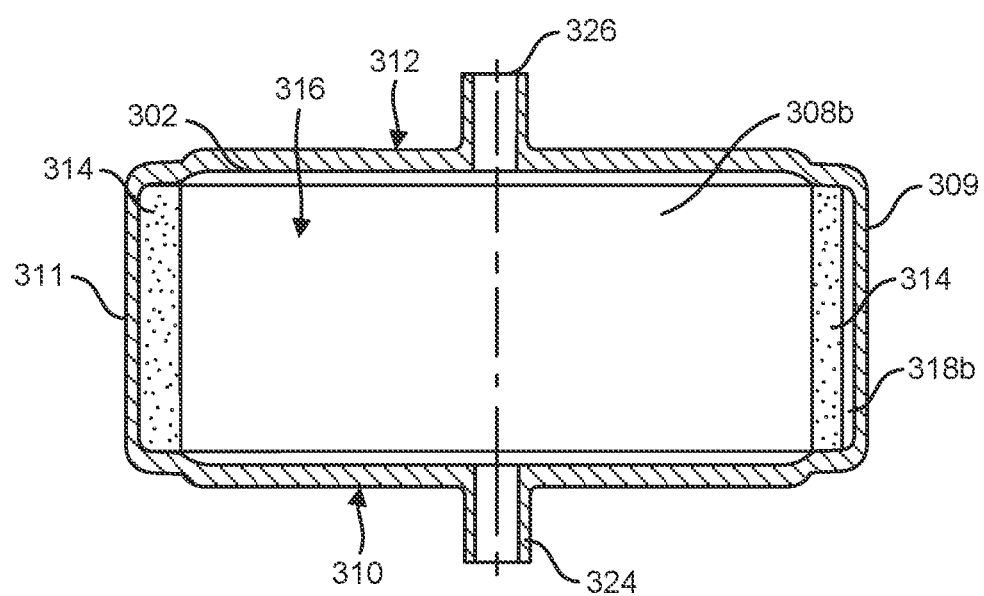
FIG. 4B is a diagram illustrating a cross-section along the lines B-B of the blood degassing module of FIG. 4, in accordance with embodiments of the subject matter of the disclosure.

The blood degassing module 300 includes a quadrilateral housing 302 (shown in cross-sections in FIGS. 4A and 4B)

having a first end cap 304 that may be integrally formed with the housing 302 or otherwise attached to one end of the housing 302, and a second end cap 306 that may be integrally formed with the housing 302 or otherwise attached to the other end of the housing 302. The housing 302 with the first end cap 304 and the second end cap 306 forms an enclosure that houses a membrane in the form of microporous hollow fibers 308 situated in the housing 302. In other embodiments, the housing 302 can be another shape, such as a pentagon or a hexagon.

The microporous hollow fibers 308 are arranged into two groups, a vertical fiber group 308a having a generally vertical orientation in the housing 302 and a horizontal fiber group 308b having a generally horizontal orientation in the housing 302.

FIG. 4A is a diagram illustrating a cross-section along the lines A-A of the blood degassing module 300 of FIG. 4, in accordance with embodiments of the subject matter of the disclosure. As illustrated in FIGS. 4 and 4A, the vertical fiber group 308a includes microporous hollow fibers 308 that extend in the vertical direction from the first end cap 304 of the housing 302 to the second end cap 306 of the housing 302.

FIG. 4B is a diagram illustrating a cross-section along the lines B-B of the blood degassing module 300 of FIG. 4, in accordance with embodiments of the subject matter of the disclosure. As illustrated in FIGS. 4 and 4B, the horizontal fiber group 308b includes microporous hollow fibers 308 that extend in the horizontal direction from one side 309 of the housing 302 to the other side 311 of the housing 302.

In some embodiments, the microporous hollow fibers 308 are stacked in the housing 302 to alternate, at 90 degree angles, between vertical fiber group bundles or fibers extending in the vertical direction and horizontal fiber group bundles or fibers extending in the horizontal direction. In other embodiments, the module 300 includes microporous hollow fibers 308 stacked or situated in the housing 302 in only one direction, such as from the first end cap 304 to the second end cap 306 or from the one side 309 to the other side 311.

The microporous hollow fibers 308 are not wound around a central core as described in relation to FIG. 3. Instead, the microporous hollow fibers 308 are forced into the housing 302 until a certain interference is reached. Also, in embodiments, the microporous hollow fibers 308 are made from or at least include one or more of PP and PMP material.

At each of the ends and sides 304, 306, 309, and 311 of the quadrilateral housing 302, the microporous hollow fibers 308 are potted with potting material 314. The microporous hollow fibers 308 in the vertical fiber group 308a are potted with potting material 314 at or adjacent each of the first and second end caps 304 and 306, and the microporous hollow fibers 308 in the horizontal fiber group 308b are potted with potting material 314 at or adjacent each of the third and fourth end caps or sides 309 and 311 of the housing 302. In embodiments, the potting material 314 includes a urethane resin.

Potting the ends of the microporous hollow fibers 308 with potting material 314 forms one blood compartment 316 configured to have blood flow through it, such that the blood contacts outer surfaces of the microporous hollow fibers 308. Potting the ends of the microporous hollow fibers 308 with potting material 314 also forms one or more compartments, such as at the end caps 304 and 306 and at the sides 309 and 311, that can be used as vacuum/sub-atmospheric pressure compartments. One such compartment is compartment 318a (shown in FIGS. 4 and 4A) that is configured to be fluidly coupled to inside surfaces of the microporous hollow fibers 308 in the vertical fiber group 308a, and another such compartment is compartment 318b (shown in FIG. 4B) that is configured to be fluidly coupled to inside surfaces of the microporous hollow fibers 308 in the horizontal fiber group 308b.

In example embodiments, one end of the microporous hollow fibers 308 in the vertical fiber group 308a and one end of the microporous hollow fibers 308 in the horizontal fiber group 308b are cut open or otherwise opened to fluidly communicate with the vacuum/atmospheric pressure compartments 318a and 318b, respectively. In other embodiments, one or both ends of the microporous hollow fibers 308 in one or both of the vertical fiber group 308a and the horizontal fiber group 308b can be cut open or otherwise opened to fluidly communicate with one or more vacuum/atmospheric pressure compartments, such as the compartments 318a and/or 318b.

In FIG. 4A, the microporous hollow fibers 308 in the vertical fiber group 308a are opened at 320, above the potting material 314 and at or adjacent the end cap 304. This fluidly couples the inside surfaces of the microporous hollow fibers 308 in the vertical fiber group 308a to the compartment 318a. The microporous hollow fibers 308 in the vertical fiber group 308a are closed off by the potting material 314 at or adjacent the other end cap 306.

In FIG. 4B, the same applies to the microporous hollow fibers 308 in the horizontal fiber group 308b, where the microporous hollow fibers 308 in the horizontal fiber group 308b are opened at one side, such as side 309, above or beyond the potting material 314, to fluidly couple the inside surfaces of the microporous hollow fibers 308 in the horizontal fiber group 308b to the compartment 318b where, in some embodiments, an external conduit (not shown) connects the open ends of the microporous hollow fibers 308 in the horizontal fiber group 308b with the open ends of the microporous hollow fibers 308 in the vertical fiber group 308a and to the compartment 318a. Thus, in some embodiments, port 322 is used to reach the inside surfaces of all of the microporous hollow fibers 308, vertically and horizontally oriented. The microporous hollow fibers 308 in the horizontal fiber group 308b are closed off by the potting material 314 at or adjacent the other side of the housing 302, such as side 311.

The microporous hollow fibers 308 are configured to pass at least some gross air and GME from blood in the blood compartment 316 to one or more of the compartments 318a and 318b.

The module 300 includes a blood inlet 324 at one side 310 of the housing 302 and a blood outlet 326 at the other side 312 of the housing 302. The blood inlet 324 and the blood outlet 326 are each fluidly coupled to the blood compartment 316. The blood inlet 324 is configured to receive blood, such as venous blood or aspirated blood, and provide the received blood to the blood compartment 316. The received blood flows through the blood compartment 316 and out of the blood outlet 326. In embodiments, the blood outlet 326 is configured to be coupled to an oxygenator for oxygenating the blood after gross air and GME have been drawn and thus removed from the blood.

The end cap 304 includes the port 322 that is fluidly coupled to the compartments 318a and 318b. The port 322 is configured to receive a vacuum or atmospheric pressure and provide it to the compartment 318a and 318b. In embodiments, the module 300 includes a relief safety valve (not shown) connected to the port 322. This relief safety valve automatically opens the compartment 318a and 318b to the to the atmosphere if for some reason the pressure becomes positive, which prevents possible inversion of the degassing action and air entering the blood.

In operation, blood mixed with some air is circulated through the blood compartment 316 from the blood inlet 324 to the blood outlet 326. In the blood compartment 316, the mixture of blood and air contacts the outer surfaces of the microporous hollow fibers 308. The inside of the microporous hollow fibers 308 is exposed to the vacuum or atmospheric pressure in the compartments 318a and 318b, such that the pressure gradient between the two sides of the microporous hollow fibers 308 causes at least some gross air and GME in the blood to cross the walls of the microporous hollow fibers 308. As a result, processed blood exiting the module 300 at the blood outlet 326 has less gross air and GME than the mixture of blood and air entering the module 300 at the blood inlet 324.

The blood degassing module 300 and the other blood degassing modules described in this disclosure are properly dimensioned to find a good balance between significant GME reduction and blood de-oxygenation. Also, in embodiments, the blood degassing modules described in this disclosure are positioned in an extracorporeal circulation circuit upstream of the oxygenator, as illustrated in FIG. 1. Also, in embodiments, the degassing modules can be used in other suitable applications.

Figure 5:
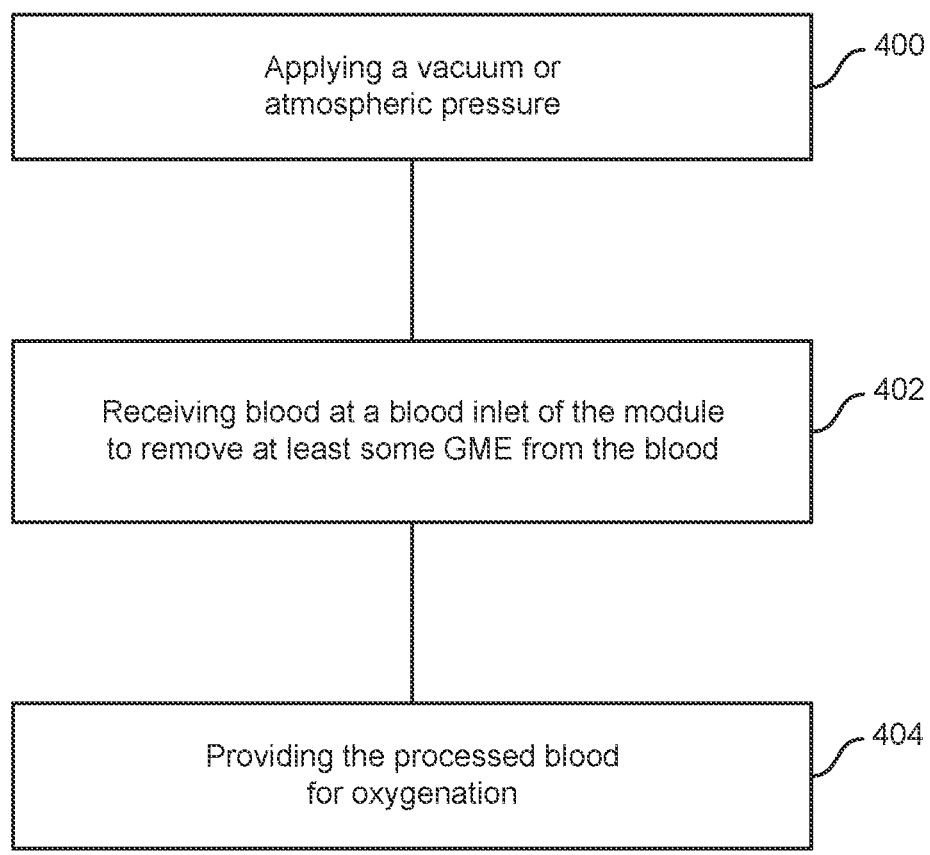
FIG. 5 is a diagram illustrating a method of processing blood to remove GME from the blood, in accordance with embodiments of the subject matter of the disclosure.

FIG. 5 is a diagram illustrating a method of processing blood to remove GME from the blood, in accordance with embodiments of the subject matter of the disclosure. In embodiments, the method includes processing the blood in a module to remove the GME from the blood prior to oxygenating the blood in an oxygenator.

At 400, the method includes applying a vacuum or atmospheric pressure at a port of the module, where the port is fluidly coupled to inside passages of microporous hollow fibers in the module. In embodiments, the port is fluidly coupled to one or more compartments in the module, which are fluidly coupled to the inside passages of the microporous hollow fibers in the module. In embodiments, the vacuum or gas at sub-atmospheric pressure or atmospheric pressure is provided from an external source, such as an external vacuum source.

At 402, the method includes receiving blood at a blood inlet of the module to remove at least some of the GME from the blood. In embodiments, receiving the blood at the blood inlet includes receiving one or more of venous blood and blood aspirated from a patient, where at least some of the GME are removed from the received blood.

The blood received at the blood inlet flows through a blood compartment in the module to a blood outlet of the module. As the blood flows through the blood compartment, the blood flows around outside surfaces of the microporous hollow fibers that are in the blood compartment. With the inside of the microporous hollow fibers receiving a vacuum or gas at atmospheric pressure, at least some of the GME in the blood are drawn from the blood through the walls of the microporous hollow fiber by the vacuum or gas at atmospheric pressure. In embodiments, the vacuum, i.e., sub-atmospheric pressures may reach −400 mmHg vacuum and more than 95% of the GME in the blood are drawn from the blood.

At 404, the method includes providing the processed blood from the module through the blood outlet for oxygenation. In embodiments this includes providing the processed blood from the module through the blood outlet to an oxygenator for oxygenation. In embodiments this includes providing the processed blood from the module through the blood outlet to the oxygenation portion of an oxygenator. In embodiments, providing the processed blood through the blood outlet includes providing processed venous blood through the blood outlet. In embodiments, the method includes receiving oxygenation gases at atmospheric pressure at the oxygenator to oxygenate the processed blood.

Figure 6:
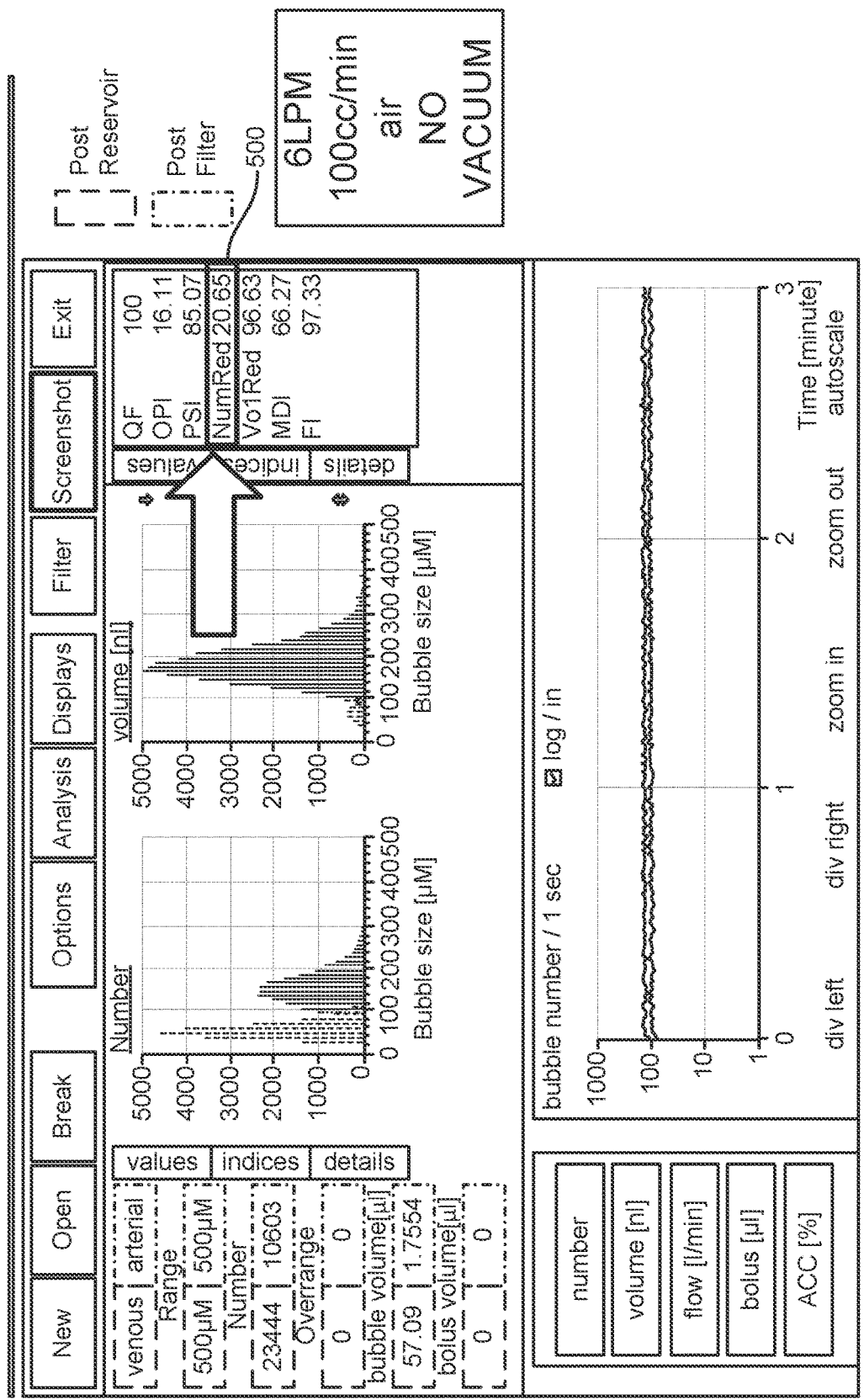
FIG. 6 is a diagram illustrating a percentage of GME removed from blood by a blood degassing module without applying a vacuum or sub-atmospheric pressure to the inside of the microporous hollow fibers.
Figure 7:
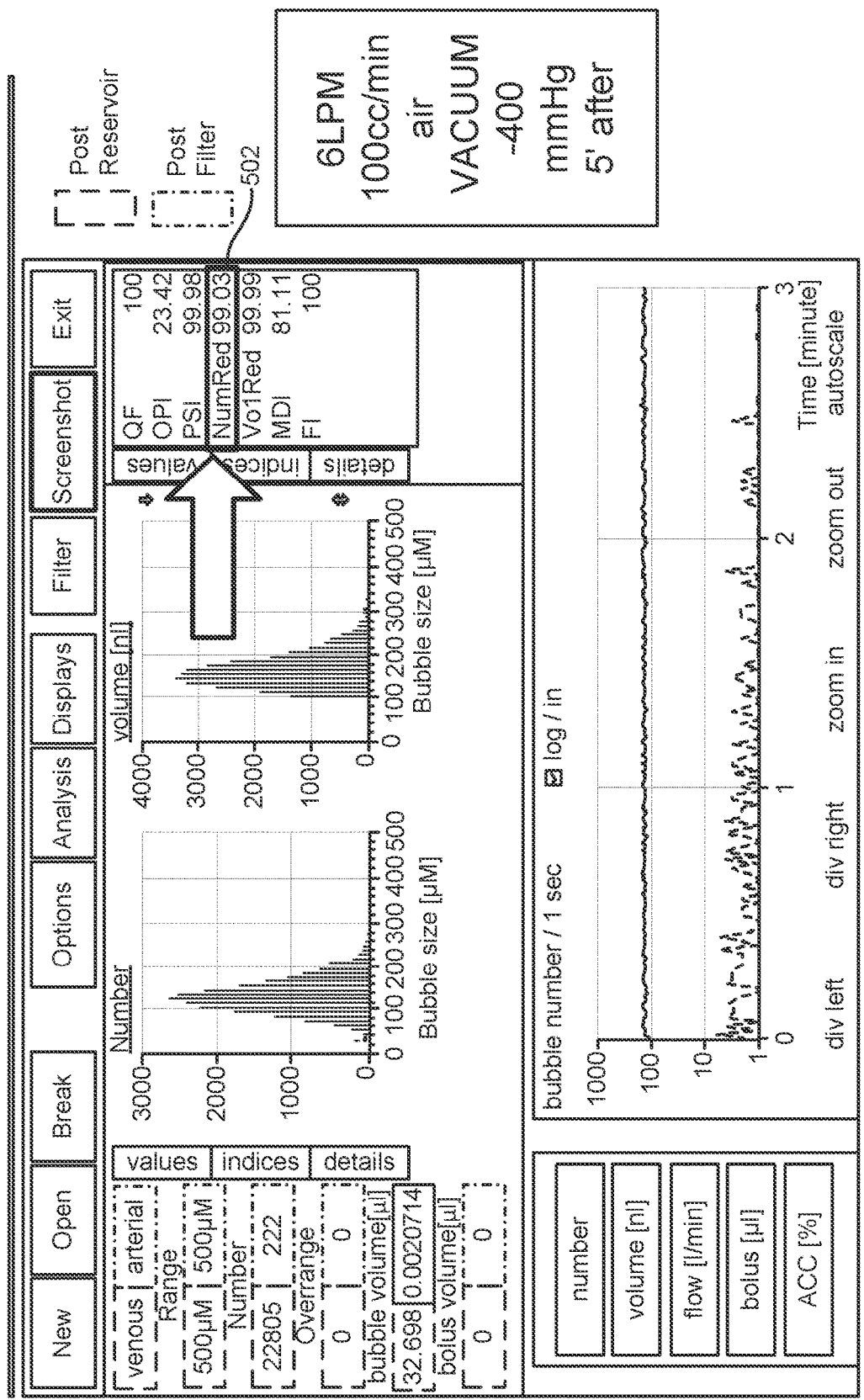
FIG. 7 is a diagram illustrating a percentage of GME removed from blood by the blood degassing module with applying a vacuum or sub-atmospheric pressure to the inside of the microporous hollow fibers, in accordance with embodiments of the subject matter of the disclosure.

FIGS. 6 and 7 are diagrams illustrating laboratory test results for a blood degassing module, in accordance with embodiments of the subject matter of the disclosure. The blood degassing module in the laboratory test is configured to have atmospheric or sub-atmospheric (vacuum) pressure applied to the inside of microporous hollow fibers and blood circulated on the outside of the microporous hollow fibers. Test results are shown in FIGS. 6 and 7.

FIG. 6 is a diagram illustrating the percentage of GME removed from the blood by the blood degassing module when applying a gas at atmospheric pressure to the inside of the microporous hollow fibers. The blood is provided to the module at 6 liters per minute (lpm) and mixed with 100 cubic centimeters per minute (cc/min) of air flow. The NumRed (GME number reduction) at 500 is in the range of 20% of the GME removed from the blood.

FIG. 7 is a diagram illustrating the percentage of GME removed from the blood by the blood degassing module with applying a vacuum or gas at sub-atmospheric pressure to the inside of the microporous hollow fibers, in accordance with embodiments of the subject matter of the disclosure. The blood is provided to the module at 6 lpm and mixed with 100 cc/min of air flow, just as illustrated in FIG. 6. The NumRed (GME number reduction) at 502 is measured 5 minutes after the application of a −400 mmHg vacuum or gas at sub-atmospheric pressure to the inside of the microporous hollow fibers. This results in a NumRed (GME number reduction) at 502 of 99%, which shows that applying a −400 mmHg vacuum or gas at sub-atmospheric pressure to the inside of the microporous hollow fibers increases the reduction of GME from the blood from 20% to 99%. Thus, the vacuum effect is evident and an ideal target of 0% GME may be approached or reached by applying an appropriate vacuum value, and based on the level of GME in the blood.

In embodiments, each of the blood degassing modules of the present disclosure can be collocated between a blood reservoir, such as a venous blood reservoir, and an oxygenator or an oxygenation portion of an oxygenator. The blood degassing module can be embodied as a standalone unit in an extracorporeal circuit, such that the gas at atmospheric or sub-atmospheric pressure is applied and controlled by a vacuum regulator and operation is independent of the oxygenator.

Alternatively, in embodiments, each of the blood degassing modules of the present disclosure can be a module integrated into the oxygenator housing inlet portion, i.e., upstream of the oxygenator and separated from it. As usually oxygenators include in the same housing a heat exchanger followed by a gas exchanger, i.e., the oxygenator itself, the blood degassing modules of the present disclosure may be collocated upstream the heat exchanger, or mixed with the heat exchanger, or downstream the heat exchanger, but always upstream the gas exchanger, such that the gas at atmospheric or sub-atmospheric pressure is controlled by a vacuum regulator and applied only to the blood degassing module portion and not to the gas side of the gas exchanger of the oxygenator.

Alternatively, in embodiments, each of the blood degassing modules of the present disclosure can be a module integrated into an outlet portion of the blood reservoir, i.e., downstream of the reservoir and upstream of the oxygenator.

Where, the gas at atmospheric or sub-atmospheric pressure is applied and controlled by a vacuum regulator and operation is independent of the blood reservoir and the oxygenator.

We claim:

1. A system for removing gaseous micro emboli from blood prior to oxygenation, the system comprising:
    a module having a blood inlet, a blood outlet, and a port configured to provide atmospheric or sub-atmospheric pressures; and
    microporous hollow fibers situated in the module and fluidly coupled to the port to provide the atmospheric or sub-atmospheric pressures inside the microporous hollow fibers,
    wherein the module is configured to receive the blood through the blood inlet such that the blood flows from the blood inlet to the blood outlet around outside surfaces of the microporous hollow fibers such that at least some of the gaseous micro emboli in the blood are drawn from the blood through the microporous hollow fibers by the atmospheric or sub-atmospheric pressures;
    wherein the module includes a housing, and the microporous hollow fibers are stacked in layers situated in the housing;
    wherein the layers of the microporous hollow fibers include vertical fiber layers and horizontal fiber layers alternating with the vertical fiber layers, wherein the vertical fiber layers cross the horizontal fiber layers at a perpendicular angle.

2. The system of claim 1, wherein the sub-atmospheric pressures include pressures down to −400 mmHg vacuum such that 95% or more of the gaseous micro emboli in the blood are drawn from the blood.

3. The system of claim 1, wherein the microporous hollow fibers are wound onto a central cylindrical core in the housing.

4. The system of claim 1, wherein the module includes housing end caps with the port situated in one end cap of the housing end caps and at least some of the microporous hollow fibers potted adjacent each of the housing end caps and open at the one end cap to fluidly couple the inside of the at least some of the microporous hollow fibers to the atmospheric or sub-atmospheric pressures provided via the port.

5. The system of claim 1, wherein the module includes at least one safety valve coupled to the port to exhaust pressures above atmospheric value.

6. The system of claim 1, further comprising an oxygenator, wherein the blood received by the module includes venous blood that is processed by the module to draw at least some of the gaseous micro emboli from the venous blood and provide the processed venous blood through the blood outlet to a gas exchanger of the oxygenator.

7. The system of claim 1, further comprising an oxygenator, wherein the module provides the blood processed by the module through the blood outlet to the oxygenator, wherein the oxygenator receives oxygenation gases at atmospheric pressure.

8. The system of claim 1, further comprising an oxygenator, wherein the module is part of a blood inlet portion of the oxygenator.

9. A system for processing blood to remove gaseous micro emboli from the blood and provide processed blood to an oxygenator that receives oxygenation gases at atmospheric pressure to oxygenate the processed blood, the system comprising:
    a module having a blood inlet at one side of the module and configured to receive the blood, a blood outlet at another side of the module and configured to output the processed blood, and a port configured to provide gas at atmospheric or sub-atmospheric pressure; and
    microporous hollow fibers situated in the module and open at one or more ends of the microporous hollow fibers to fluidly couple inside passages of the microporous hollow fibers to the port,
    wherein the module receives the blood through the blood inlet and the blood flows from the blood inlet to the blood outlet and around outside surfaces of the microporous hollow fibers to draw at least some of the gaseous micro emboli from the blood through the microporous hollow fibers;
    wherein the module includes a housing, and the microporous hollow fibers are stacked in layers at least one of horizontally and vertically situated in the housing;
    wherein the microporous hollow fibers are stacked in layers with the microporous hollow fibers in each layer crossing the microporous hollow fibers in an adjacent layer at an angle in the housing.

10. The system of claim 9, wherein the module includes housing end caps with the port situated in one end cap of the housing end caps and the microporous hollow fibers potted near each of the housing end caps and open at the one end cap to fluidically couple the inside passages of the microporous hollow fibers to the gas at atmospheric or sub-atmospheric pressure.

11. The system of claim 9, wherein the microporous hollow fibers are wound around a central core in the housing.

12. The system of claim 9, wherein the gas at sub-atmospheric pressure reaches −400 mmHg vacuum, such that 95% or more of the gaseous micro emboli in the blood are drawn from the blood.

13. The system of claim 9, wherein the layers of the microporous hollow fibers include vertical fiber layers and horizontal fiber layers alternating with the vertical fiber layers, wherein the vertical fiber layers cross the horizontal fiber layers at a perpendicular angle.

* * * * *